(12) United States Patent
Takeuchi et al.

(10) Patent No.: US 7,286,226 B2
(45) Date of Patent: Oct. 23, 2007

(54) METHOD AND APPARATUS FOR MEASURING BIREFRINGENCE

(75) Inventors: Seiji Takeuchi, Utsunomiya (JP); Yasuhiro Kishikawa, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 292 days.

(21) Appl. No.: 10/733,359

(22) Filed: Dec. 12, 2003

(65) Prior Publication Data

US 2004/0156051 A1    Aug. 12, 2004

(30) Foreign Application Priority Data

Dec. 13, 2002 (JP) ............................. 2002-362251
Nov. 19, 2003 (JP) ............................. 2003-389419

(51) Int. Cl.
*G01J 4/00* (2006.01)
(52) U.S. Cl. ..................................... 356/364
(58) Field of Classification Search ................ 356/364, 356/369
See application file for complete search history.

(56) References Cited

U.S. PATENT DOCUMENTS

| 4,681,450 | A | 7/1987 | Azzam |
| 5,298,972 | A | 3/1994 | Heffner |
| 5,517,589 | A | 5/1996 | Takeuchi |
| 5,784,202 | A | 7/1998 | Noguchi |
| 6,266,141 | B1 * | 7/2001 | Morita ........................ 356/365 |

2003/0234348 A1    12/2003   Takeuchi et al.

FOREIGN PATENT DOCUMENTS

| EP | 0 536 538 | 4/1993 |
| EP | 0 597 390 | 5/1994 |
| FR | 2 839 551 | 11/2003 |
| JP | 05-209791 | 8/1993 |
| JP | 08-201175 | 8/1996 |
| WO | WO 02/12947 | 2/2002 |

OTHER PUBLICATIONS

Umeda, et al., "Measurement of the Residual Birefringence Distribution in Glass Laser Disk by Transverse Zeeman Laser", Electronics and Communication in Japan, Part 2, vol. 74, No. 5, pp. 21-28 (1991).
Wang, et al., "A New Instrument for Measuring Both the Magnitude and Angle of Low Level Linear Birefringence," Review of Scientific Instruments, vol. 70, No. 10, pp. 3847-3854 (1999).
Nikolova, et al., "Photoinduced Anisotropy: New Photopolarimetric Setup for Real-Time Measurements," Applied Optics, vol. 31, No. 31, pp. 6698-6701, (1992).

* cited by examiner

*Primary Examiner*—Roy M. Punnoose
(74) *Attorney, Agent, or Firm*—Fitzpatrick, Cella, Harper & Scinto

(57) ABSTRACT

Disclosed is a birefringence measuring apparatus and method for measuring birefringence of a sample in a reduced time and in a simple manner. The birefringence measuring apparatus includes a light projecting unit for projecting approximately circularly polarized light upon a sample, a Stokes meter for detecting a state of polarization of light from the sample, and a calculating system for calculating birefringence of the sample on the basis of a Stokes parameter from the Stokes meter.

7 Claims, 4 Drawing Sheets

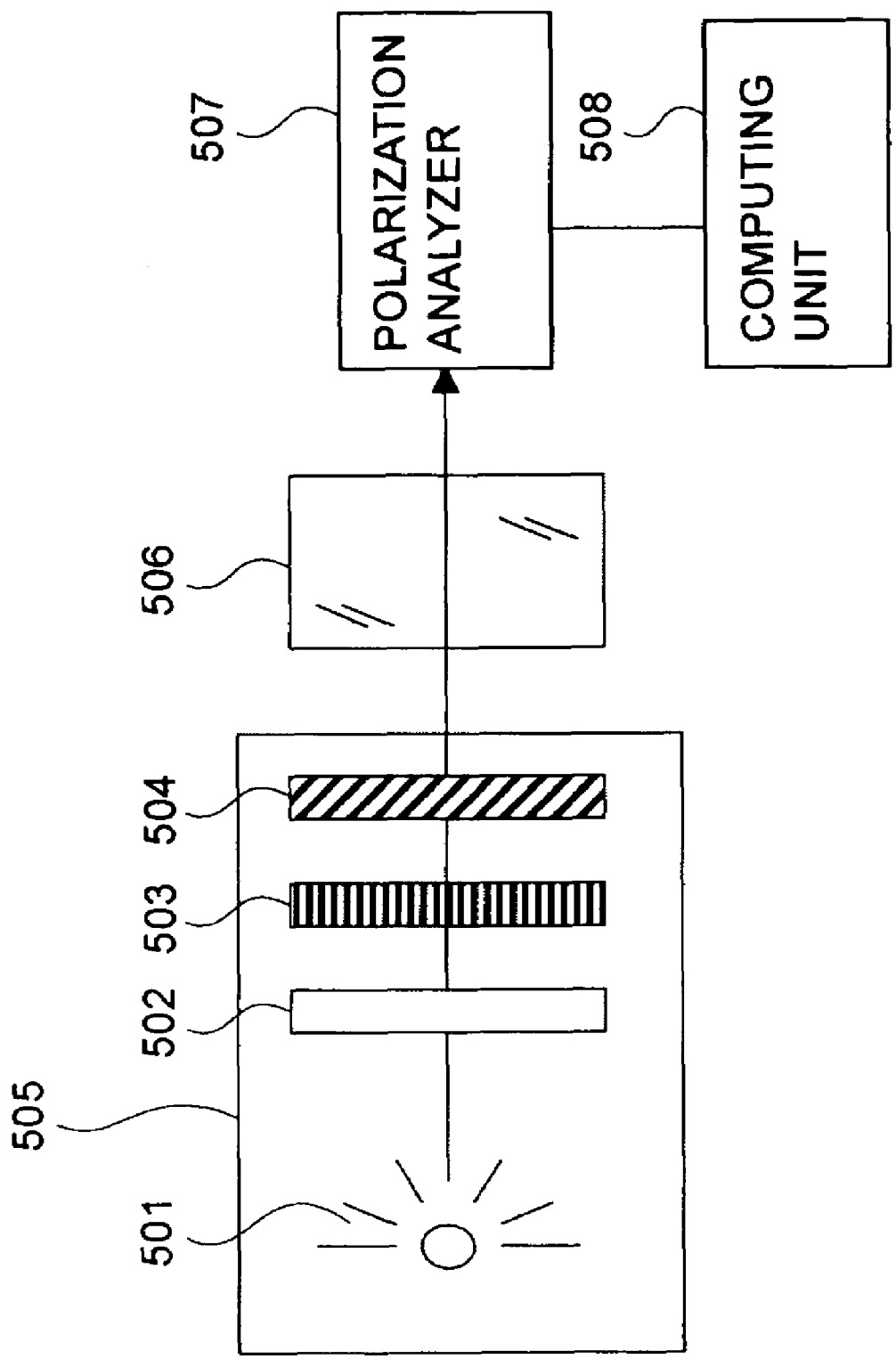

US 7,286,226 B2

METHOD AND APPARATUS FOR MEASURING BIREFRINGENCE

FIELD OF THE INVENTION AND RELATED ART

This invention relates to a birefringence measuring method and apparatus for measuring birefringence of a sample.

Birefringence measuring apparatuses are known in the art, and an example is one based on a phase measuring method using a heterodyne light source, such as discussed in "Measurement of the Residual Birefringence Distribution in Glass Laser Disk by Transverse Zeeman Laser", N. Umeda and H. Kohwa, Electronics and Communications in Japan, Part 2, Vol. 74, No. 5 (1991), pp21-28. Also, a birefringence measuring apparatus based on a phase modulation device is known, as discussed in "A new instrument for measuring both the magnitude and angle of low level linear birefringence", B. Wang & T. C. Oakberg, Review of Scientific Instruments, Vol. 70, No. 10 (1999), pp3847-3854.

On the other hand, apparatuses called a "Stokes meter", "polari-meter" or "polarization analyzer" are currently commercially available, and they can be roughly categorized into two types. One type is such that a light beam whose polarization state is going to be detected is separated into plural light beams which are then received by polarizing elements, respectively, and the polarization state is detected on the basis of the light quantities of different polarization components, as disclosed in Japanese Laid-Open Patent Application No. H5-209791 (corresponding to U.S. Pat. No. 5,298,972) or Japanese Laid-Open Patent Application No. H8-201175). The other type is such that measurement light is detected through a rotating element, and generally this is called a rotation analyzer method.

In conventional birefringence measuring apparatuses as described above, the state of polarization of light from a sample is measured plural times while changing the polarization of light impinging on the sample, and the birefringence of the sample is measured on the basis of the results of plural measurements. In conventional birefringence measuring apparatuses, although some of them use a rotary element at a side receiving polarized light from a sample while others do not use such element, there is a rotary element or the like at a light entrance side of the sample that must be rotated to change the polarization of light impinging on the sample. As a result, a long time is required to complete the birefringence measurement.

For this reason, where the amount of birefringence changes radically, the measurement is difficult to accomplish. Further, where the light source is a pulse light source or the output thereof is unstable, the measurement is difficult to complete.

SUMMARY OF THE INVENTION

It is accordingly an object of the present invention, as an example, to provide a birefringence measuring apparatus by which at least one of the problems discussed above can be solved and by which birefringence can be measured in a reduced time.

In accordance with an aspect of the present invention, there is provided a birefringence measuring apparatus, comprising: a light projecting unit for projecting approximately circularly polarized light upon a sample; a Stokes meter for detecting a state of polarization of light from the sample; and calculating means for calculating birefringence of the sample on the basis of a Stokes parameter from said Stokes meter.

In accordance with an aspect of the present invention, there is provided a birefringence measuring apparatus, comprising: a light projecting unit for projecting approximately circularly polarized light upon a sample; a Stokes meter for detecting a state of polarization of light from the sample; and calculating means for calculating birefringence of the sample on the basis of a Stokes parameter from the Stokes meter.

In accordance with another aspect of the present invention, there is provided a birefringence measuring apparatus, comprising: a light projecting unit for projecting approximately circularly polarized light upon a sample; a plurality of light receiving portions for detecting a light quantity of light from the sample; and calculating means for determining a Strokes parameter on the basis of detected values at the plurality of light receiving portions, and for detecting birefringence of the sample on the basis of the Stokes parameter.

In accordance with a further aspect of the present invention, there is provided a birefringence measuring apparatus, comprising: a light projecting unit for projecting approximately circularly polarized light upon a sample; a plurality of light receiving portions for detecting a light quantity of light from the sample; a memory for memorizing birefringence measured by the birefringence measuring apparatus without a sample; and calculating means for detecting birefringence of the sample on the basis of detected values at the plurality of light receiving portions and the birefringence memorized by the memory.

In accordance with a yet further aspect of the present invention, there is provided a birefringence measuring apparatus, comprising: light projecting means for projecting approximately circularly polarized light upon a sample; at least one dividing unit for dividing output light from the sample into two light beams having the same polarization state; at least one polarizer; at least one phase-difference plate; at least two light receiving portions; and calculating means for calculating a quantity of received light at the at least two light receiving portions.

In accordance with a still further aspect of the present invention, there is provided a birefringence measuring apparatus, comprising: light projecting means for projecting approximately circularly polarized light upon a sample; at least one dividing unit for dividing output light from the sample into two light beams having the same polarization state; at least one polarizer; at least four light receiving portions; and calculating means for calculating a quantity of received light at the at least four light receiving portions, wherein the birefringence of the sample is measured without rotating the sample and the at least one polarizer.

In accordance with another aspect of the present invention, there is provided a birefringence measuring apparatus, comprising: light projecting means for projecting approximately circularly polarized light upon a sample; at least two dividing units for dividing output light from the sample into two light beams having the same polarization state; and four light receiving portions, wherein a first light beam having the same polarization state as the output light from the sample is incident on one polarization dividing means whereby the first light beam is divided into two light beams having two orthogonal polarization components which beams are received by light receiving portions, respectively, wherein, regarding a second light beam having the same polarization state as the output light from the sample, a polarization component different by 45 deg. from the two orthogonal polarization components is detected by a light receiving portion through a polarizer, and wherein, regarding a third light beam having the same polarization state as the output light from the sample, only a circular polarization component is detected by a light receiving portion through a phase-difference plate and a polarizer, whereby the amount of birefringence of the sample is measured.

In accordance with a further aspect of the present invention, there is provided a birefringence measuring apparatus, comprising: light projecting means for projecting approximately circularly polarized light upon a sample; at least three dividing units for dividing output light from the sample into two light beams having the same polarization state as the light from the sample; and four light receiving portions, wherein a first light beam having the same polarization state as the output light from the sample is incident on a first polarizer, and a first polarization component is detected by a first light receiving portion, wherein a second light beam having the same polarization state as the output light from the sample is incident on a polarizer, and a second polarization component orthogonal to the first polarization component is detected by a second light receiving portion, wherein a third light beam having the same polarization state as the output light from the sample is incident on a polarizer, and a third polarization component being different by 45 deg. from the first polarization component is detected by a third light receiving portion, and wherein a fourth light beam having the same polarization state as the output light from the sample is incident on a phase-difference plate and a polarizer, and a circular polarization component is detected by a fourth light receiving portion, wherein the amount of birefringence of the sample is measured.

In accordance with a yet further aspect of the present invention, there is provided a method of measuring birefringence, comprising the steps of: projecting approximately circularly polarized light upon a sample; detecting a light quantity of light from the sample; determining a Stokes parameter on the basis of the detection of the light quantity; and detecting birefringence of the sample on the basis of the Stokes parameter.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 5 is a schematic view of a main portion of a birefringence measuring apparatus according to another embodiment of the present invention.

DESCRIPTION OF THE PREFERRED EMBODIMENTS

Preferred embodiments of the present invention will now be described with reference to the attached drawings.

Embodiment 1

A first embodiment of the present invention will be described with reference to FIGS. 1 and 2.

Figure 1:
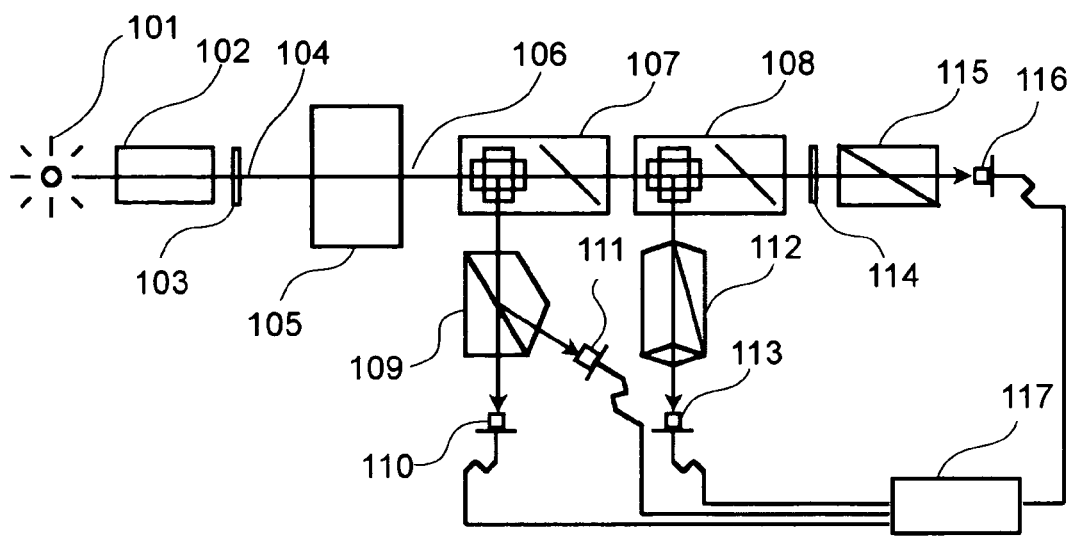
FIG. 1 is a schematic view of a main portion of a birefringence measuring apparatus according to an embodiment of the present invention.

Denoted in FIG. 1 at 101 is a light source, and denoted at 102, 112 and 115 each is a single-light-beam type Glan-Thompson polarization prism. Denoted at 103 and 114 are quarter ($\lambda/4$) phase difference plates, and denoted at 104 is incident light projected on a sample 105 whose birefringence is going to be measured. Denoted at 106 is output light emerging from the sample 105. Denoted at 107 and 108 are dividing units each for dividing light incident thereon into two light beams having the same polarization state as the incident light, the dividing unit then outputting the divided light beams. Denoted at 109 is a dual-light-beam type Glan-Thompson polarization prism, and denoted at 110, 111, 113 and 116 are light receiving portions. Denoted at 117 is calculating or computing means.

Light from the light source 101 passes through the polarization prism 102 whereby it is transformed into linearly polarized light. Thereafter, the light goes through the quarter phase plate 103 having a phase advance axis tilted by +45 deg. with respect to a horizontal axis, by which the incident light 104 is transformed into right-handed circular polarization light. Here, the light source 101, the polarization prism 102 and the quarter phase plate 103 constitute a light projecting unit. A circularly polarized light from this light projecting unit is incident on a sample 105. Under the influence of birefringence of the sample 105, the output light 106 emerging from the sample 105 is generally elliptically polarized light, and it enters the dividing unit 107. The output light is divided thereby into a first light beam being reflected under the same polarization state as the output light 106 and a second light beam being transmitted under the same polarization state as the output light 106. The first light beam enters a dual-beam type Glan-Thompson prism 109 whereby it is divided into two light beams being polarized orthogonally. The divided light beams are then incident on the light receiving portions 110 and 111, respectively. The second light beam transmitted through the dividing unit 107 furthermore enters the dividing unit 108 whereby it is divided into a third light beam being reflected again under the same polarization state as the output light 106 and a fourth light beam being transmitted under the same polarization state as the output light 106. The third light beam is then incident on a single-beam type Glan-Thompson prism 112 having its transmission axis rotated by and fixed at +45 deg. such that a +45 deg. linear polarization component is received by the light receiving portion 113. The fourth light beam is incident on a quarter ($\lambda/4$) phase difference plate 114 having its advance axis rotated by and fixed at +45 deg., and thereafter it is incident on a single-beam type Glan-Thompson prism 115 having its transmission axis fixed at 90 deg., such that only the transmitted polarization component is detected by the light receiving portion 116. On the basis of the detected values of light quantities as detected by the light receiving portions 110, 111, 113 and 116, the computing circuit 117 calculates to detect the Strokes parameters.

Figure 2:
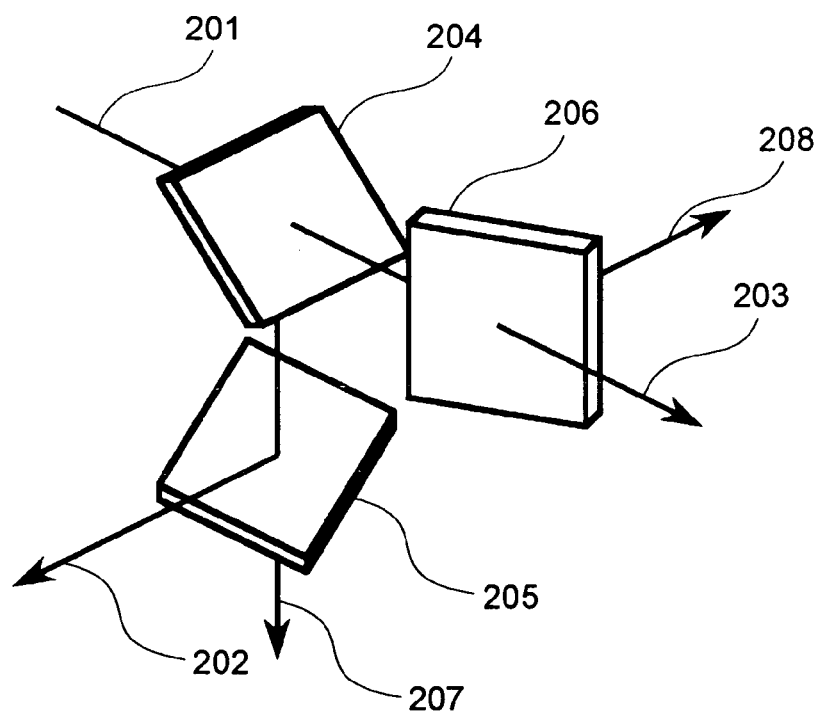
FIG. 2 is a schematic view of a light dividing unit in an embodiment of the present invention.

Referring to FIG. 2, a light dividing unit for conserving the polarization state will be explained.

FIG. 2 illustrates a dividing unit for dividing incident light, being incident thereon, into two light beams having the same polarization state as the incident light, and then for outputting the divided light beams.

Denoted at 201 is incident light, and denoted at 204, 205 and 206 are plain parallel plates disposed so that light is incident thereon with an angle 45 deg. Denoted at 202 is a first light beam reflected twice by two plane parallel plates, and denoted at 203 is a light beam transmitted through both of two plane parallel plates. Denoted at 207 and 208 are unwanted light, not used in this embodiment.

The first and second plane parallel plates 204 and 205 are disposed so that a p-polarized component reflected by the first plane parallel plate 204 is reflected by the second plane parallel plate as an s-polarized component. With this structure, the polarization component reflected as s-polarized light by the first plane parallel plate 204 is reflected as p-polarization component by the second plan parallel plate 205.

On the other hand, the third plane parallel plate 206 is disposed so that the p-polarized component transmitted through the first plane parallel plate 204 is transmitted as s-polarization component by the third plane parallel plate 206. With this structure, the polarization component being transmitted as s-polarized light through the first plane parallel plate 204 is reflected as p-polarization component by the third plane parallel plate 206.

Next, the principle for dividing incident light into two light beams under the same polarization state will be explained. For simplicity in explanation, reflection at the bottom face of the plane parallel plate is ignored.

If the incident light beam is perfect polarization light, its field vector will be $$E = E_p + E_s,$$

and it can be calculated separately as a linear polarization component Ep that provides p-polarized component upon reflection by the first plane parallel plate and as a linear polarization component Es that provides s-polarized component. Even where the incident light is partial polarization light or non-polarization light, since these lights can be regarded as aggregation of plural perfect polarization components, the respective perfect polarization lights may well be conserved.

Where three plane parallel plates made of the same material are used, p-polarized light and s-polarized light of the three plane parallel plates have the same complex amplitude reflectance $r_p$ and $r_s$. Therefore, if the complex amplitude of the linear polarization component of the incident light that provides p-polarization component upon reflection by the first plane parallel plate is $E_p$ while the complex amplitude of the s-polarization component is $E_s$, the complex amplitude $E_{11}$ of the first polarization component of the first light beam 202 obtained by double reflections is given by $$E_{11} = r_s r_p E_p.$$

On the other hand, the complex amplitude $E_{12}$ of the second polarization component is given by $$E_{12} = r_p r_s E_s.$$

The complex amplitude E1 of the reflection light, corresponding to the sum of them, is $$E_1 = r_s r_p (E_p + E_s).$$

This is a mere product of incident light by constants $r_s$ and $r_p$. Therefore, it is seen that the first light beam 202 has the same polarization state as the incident light.

On the other hand, the complex amplitude $E_{21}$ of the first polarization component of the second light beam 203 obtained by double transmissions is given by $$E_{21} = t_s t_p E_p.$$

On the other hand, the complex amplitude $E_{22}$ of the second polarization component is given by $$E_{22} = t_p t_s E_s.$$

The complex amplitude $E_2$ of the transmitted light, corresponding to the sum of them, is $$E_2 = t_s t_p (E_p + E_s)$$

This is a mere product of incident light by constants $t_s$ and $t_p$. Therefore, it is seen that the second light beam 203 has the same polarization state as the incident light.

In this example, light is incident on the plane parallel plate at an angle 45 deg. However, if the incidence angle to the three plates is the same, the angle may be any other than 45 deg. Further, where three elements such as gratings or beam splitters having a light dividing function and having the same dividing characteristic such as reflection characteristic or transmission characteristic with respect to polarized light, are used, similar advantageous results are obtainable. The constants $r_p$, $r_s$, $t_p$, $t_s$ are not limited to mere real number constants. Where a splitter having a film is used, for example, they may be complex number-constants that represent a change of phase.

Although unwanted light is not illustrated in FIG. 1, the light beams 207 and 208 in FIG. 2 are stray lights, and they may be absorbed by a beam damper, for example.

In FIG. 1, usually, the output light being influenced by birefringence of the sample is elliptically polarized light. The computing means 117 calculates the quantity of light from four detectors in the following manner, and it detects the Stokes parameters representing the polarization state of the elliptical polarization of the output light. In this example, it is assumed that the two light dividing units 107 and 108 have the same characteristic and that the incident light and the output light have an interrelation as described above. Also, it is assumed that the Glan-Thompson prism and the phase plate have a transmissivity of 100%. The complex amplitudes $E_A$, $E_B$, $E_C$ and $E_D$ of the electric fields of light beams obtainable at the light receiving portions are given by $$E_A = r_p r_s E_s$$

$$E_B = r_s r_p E_p$$

$$E_C = \frac{1}{\sqrt{2}} r_s r_p t_s t_p (E_p + E_s)$$

$$E_D = \frac{1}{\sqrt{2}} t_s^2 t_p^2 e^{\frac{\pi}{2}i} \left( e^{-\frac{\pi}{4}i} E_s + e^{\frac{\pi}{4}i} E_p \right)$$

Thus, the light quantities $I_1$, $I_2$, $I_3$ and $I_4$ to be detected by the light receiving portions 110, 111, 113 and 116, respectively, are given by $$I_1 = |r_p r_s|^2 |E_s|^2$$

$$I_2 = |r_s r_p|^2 |E_p|^2$$

$$I_3 = \frac{1}{2}|r_s r_p t_s t_p|^2 |E_s + E_p|^2$$

$$I_4 = \frac{1}{2}|t_s t_p|^4 \left| e^{-\frac{\pi}{4}i} E_s + e^{\frac{\pi}{4}i} E_p \right|^2$$

The constants rp, rs, tp and ts may be detected beforehand by calculation or measurement, and correcting calculation may be performed for these constants. In the calculating means 117, the following equations are carried out to detect the Stokes parameters $S_0$ (total light quantity), $S_1$ (horizontal linear polarization component), $S_2$ (+45 deg. linear polarization component), and $S_3$ (right-handed circular polarization component).

$$S_0 = (I_1 + I_2)/|r_p r_s|^2$$

$$S_1 = (I_1 - I_2)/|r_p r_s|^2$$

$$S_2 = 2 * I_3 / |r_p r_s t_p t_s|^2 - S_0$$

$$S_3 = 2 * I_4 / |t_p t_s|^4 - S_0$$

When the Stokes parameters are calculated in the above-described manner, all the information regarding the polarization state, including the quantity of light, can be obtained.

Figure 6A:
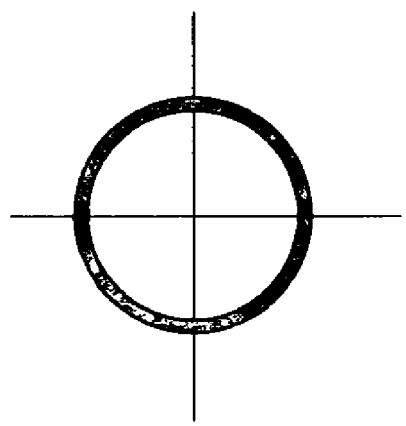
FIG. 6A is a schematic view for explaining a polarization state of light incident on s sample, in an embodiment of the present invention.
Figure 6B:
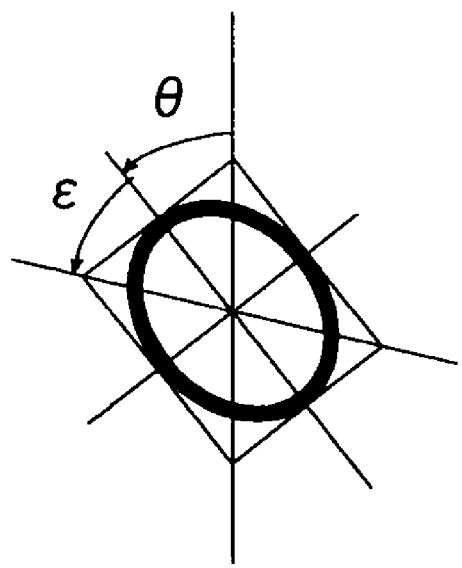
FIG. 6B is a schematic view for explaining a polarization state of light from a sample, in an embodiment of the present invention.

Referring to FIGS. 6A and 6B, the relation between the output light and birefringence will be explained. The output light is an elliptical light being tilted as shown in FIG. 6A in accordance with the phase advance axis angle and the birefringence amount of the sample. Here, the tilt of the major axis is θ, and the angle defined, with respect to the major axis angle, by a diagonal of an oblong that the ellipse circumscribes is ε. The tilt of the major axis has the following relationship with respect to the advance axis angle φ of birefringence, and the ellipticity of the ellipse has the following relation with the birefringence amount B.

$$B = \frac{\pi}{2} - 2\varepsilon$$

$$\phi = \theta - \frac{\pi}{4}$$

Also, where ε and θ are expressed in terms of Stokes parameters, the following relations are provided.

$$\varepsilon = \frac{1}{2}\arcsin\left(\frac{S_3}{S_0}\right)$$

$$\theta = \frac{1}{2}\arctan\left(\frac{S_2}{S_1}\right)$$

In the computing means 117, the following calculations are carried out furthermore, to detect the birefringence.

While in this example a Glan-Thomson prism is used as the element 109, any other optical element may be used provided that it has a function for dividing orthogonal polarization components. Examples are a Rochon prism, a Senarmont prism, a Wollaston prism, a polarization beam splitter made by use of a dielectric multilayered film, and so on. However, depending on that which polarization component is detected and which detector detects it, the calculation may be different from the forgoing description.

Further, although Glan-Thomson prisms are used also for the elements 112 and 115, any other optical element may be used, provided that it has a function for extracting a linear polarization component. Where a Brewster window or a sheet-type polarizing plate is used as the polarization element, an inexpensive apparatus can be constructed.

In the birefringence measuring apparatus of this embodiment, since there is no necessity of providing a rotary element at the light entrance side of the sample as in the conventional structures, there is an advantage that the birefringence measurement can be accomplished in a shortened time and in a simple manner. Furthermore, the size of the apparatus itself does not increase.

Embodiment 2

A second embodiment of the present invention is as follows. In the measuring apparatus shown in FIGS. 1 and 2, in place of dividing the light beam into two at 109, a polarizing element for extracting a linearly polarized component is used. On the other hand, before the dividing unit 107, an additional dividing unit of the same structure is provided to separate another light beam having the same polarization state as the output light from the sample. Polarizing element and detector are provided so as to extract a linear polarization component orthogonal to the linear polarization component to be detected at 109. This method is particularly effective to a case where two high-precision polarization prisms are used to accurately extract the linear polarization component.

Embodiment 3

A third embodiment of the present invention concerns a birefringence measuring apparatus in which a pulse light source is used as the light source. In FIG. 1, the light source 101 is now a pulse light source. As for extreme ultraviolet light or vacuum ultraviolet light, a pulse light source such as an ArF excimer laser or F2 excimer laser is used. While the data processing is similar to that of the first embodiment, signals obtained by four light receiving portions are processed synchronously, by which birefringence can be measured with respect to each pulse, without being dependent upon changes in the light quantity of the light source. Further, the sample and the optical system are relatively moved relative to each other, by which a two-dimensional distribution of the birefringence of the sample can be measured.

Embodiment 4

A fourth embodiment of the present invention concerns a structure in which, in the birefringence measuring apparatus of the first embodiment, the light receiving portion comprises an area (two-dimensional) sensor. The area sensor may be a CCD camera, for example. A collimator is used to expand the light from the light source, substantially into a parallel light. Also, a polarization prism and a phase difference plate, with which uniform characteristic is obtainable along a plane, are used. The pixels of the CCD camera are adjusted so that four corresponding detectors measure the same position. With the respective pixels, four Stokes parameters are obtained and, by detecting respective birefringence amounts and advance axis azimuths, a two-dimensional distribution of birefringence of the sample can be detected.

Embodiment 5

Figure 3:
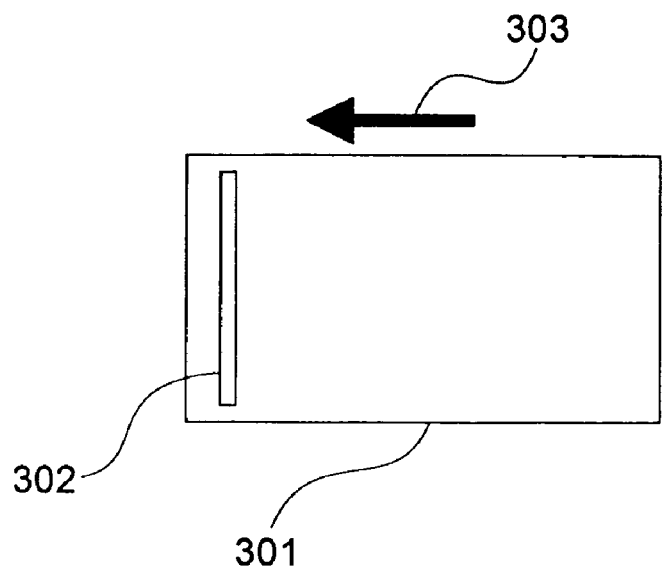
FIG. 3 is a schematic view for explaining scan of sample and a measurement region, in an embodiment of the present invention

A fifth embodiment of the present invention is such that, in the birefringence measuring apparatus of the first embodiment, the light receiving portion comprises a linear (one-dimensional) sensor. As regards the one-dimensional sensor, a one-dimensional CCD array may be used, for example. A collimator is used to expand the light from the light source, substantially into parallel light. Before a phase plate and a polarizing prism as circular polarization transforming means at the light projecting side as well as the light receiving units at the light receiving side, there are polarization prisms and phase difference plates with which uniform characteristic is obtainable along a plane. The pixels of the CCD array are adjusted so that four corresponding detectors measure the same position. With the respective pixels, four Stokes parameters are detected and, by detecting the birefringence amount and advance axis azimuth, the birefringence of the sample in a linear-shape region can be detected. In FIG. 3, denoted at 301 is a sample, and denoted at 302 is a linear-shape measurement region. Denoted at 303 is the sample scan direction. By moving the sample relative to the linear-shape measurement region, a two-dimensional distribution of birefringence can be measured. Since relative motion of the sample and the measurement region is required, similar advantageous results are obtainable by moving the light projecting portion and the light receiving portion while holding the sample fixed.

As regards the sample scanning method, stepwise motion or continuous constant-speed motion is usable. An appropriate scan method and scan speed can be chosen in accordance with the CCD integration time and the type of the light source used (continuous emission light source or pulse light source, for example).

Embodiment 6

Figure 4:
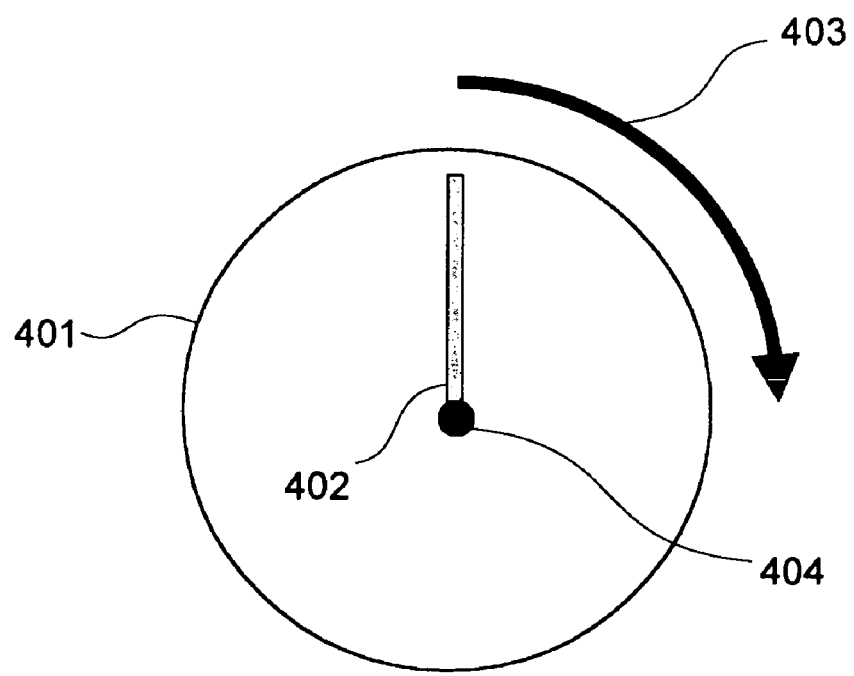
FIG. 4 is a schematic view for explaining rotation of a sample and a measurement region, in an embodiment of the present invention.

A sixth embodiment of the present invention is an example wherein the apparatus of the fifth embodiment is applied to a circular sample. By rotation, a circular measurement region is provided. In FIG. 4, denoted at 401 is a sample, and denoted at 402 is a linear-shape measurement region. Denoted at 403 is the sample rotating direction, and denoted at 404 is the center of rotation. The linear-shape measurement region is defined along a radial direction from the rotational center of the sample and, by rotating the sample about the rotational center 404, a two-dimensional distribution of birefringence of the sample is measured. This is suitable to birefringence measurement of a rotating disk. Relative rotation between the sample and the measurement region is a requirement, in this example. Therefore, if rotation of the sample is undesirable, the sample may be held fixed and the light projecting portion and the light receiving portion may be rotated. This enables measurement of a two-dimensional distribution of the birefringence amount of a circular sample and the advance axis angle, without rotating the sample.

Embodiment 7

FIG. 5 illustrates a seventh embodiment of the present invention. There is a light source 501 inside a light projecting unit 505. Light from the light source goes through a filter 502, a polarization plate 503, and a quarter (λ/4) phase difference plate 504, for example, and it is incident on a sample 506 as circularly polarized light of a desired wavelength. A polarization analyzer 507 detects output light from the sample, and it produces and applies an output to a computing circuit 508.

A light source for ultraviolet light may be a D2 lamp, but instead a laser may be used, for example. The filter 502 is a wavelength selecting filter, and it functions to select and transmit light of a predetermined wavelength, out of the light from the light source. A wavelength such as 248 nm, 193 nm or 157 nm, for example, suitable for measurement of the birefringence of the sample is selected. In place of the filter, a spectroscope may be used. As regards the polarization plate 503, although a film type may be used for visible light, a Glan laser prism or Rochon prism may be used for ultraviolet light. As regards the waveplate 504, in many cases, a crystal type such as quartz crystal or magnesium fluoride, for example, may be used for the ultraviolet light. The polarization plate provides linearly polarized light, and by using a quarter phase plate having its advance axis rotated by 45 deg. with respect to the linearly polarized light, the output light is transformed into circularly polarized light.

Thus, the light impinging on the sample is circularly polarized light. Referring to FIG. 3, the relation between the output light and birefringence will be explained. The output light is an elliptical light being tilted as shown in FIG. 3 in accordance with the phase advance axis angle and the birefringence amount of the sample. Here, the tilt of the major axis is θ, and the angle defined, with respect to the major axis angle, by a diagonal of an oblong that the ellipse circumscribes is ε. The tilt of the major axis has the following relationship with respect to the advance axis angle φ of birefringence, and the ellipticity of the ellipse has the following relation with the birefringence amount B.

$$B = \frac{\pi}{2} - 2\varepsilon$$

$$\phi = \theta - \frac{\pi}{4}$$

To this elliptically polarized light, measurement is carried out by using the polarization analyzer. Where the Stokes parameters $S_0$, $S_1$, $S_2$ and $S_3$ are detected by means of the polarization analyzer, if ε and θ are expressed in terms of Stokes parameters, the following relations are provided.

$$\varepsilon = \frac{1}{2}\arcsin\left(\frac{S_3}{S_0}\right)$$

$$\theta = \frac{1}{2}\arctan\left(\frac{S_2}{S_1}\right)$$

Thus, the computing means processes the parameters from the polarization analyzer, and detects the birefringence, as follows.

$$B = \frac{\pi}{2} - \arcsin\left(\frac{S_3}{S_0}\right)$$

$$\phi = -\frac{\pi}{4} + \frac{1}{2}\arctan\left(\frac{S_2}{S_1}\right)$$

While in this example a Stokes meter is used as the polarization analyzer 507, any other polarization analyzer means, other than the Stokes meter, may be used to detect the ellipticity ε and tilt θ of the ellipse.

The sample is placed on an X-Y stage, for example, and after the birefringence of the sample is measured with respect to a certain position, the X-Y stage may be moved to repeat the birefringence measurement. A two-dimensional birefringence distribution of the sample can be measured in this manner.

As regards the polarization analyzer, there are many varieties as discussed in relation to the prior art. One discussed with reference to the first embodiment is an example.

Embodiment 8

An eighth embodiment of the present invention concerns removal of apparatus errors. As regards the phase plate 504 used in the seventh embodiment, products having good qualities with respect to light of a wavelength not greater than 370 nm (more particularly, not greater than 200 nm), such as 248 nm, 193 nm or 157 nm, for example, are very expensive. It is very difficult to obtain a phase plate that provides perfect $\lambda/4$ without an error. Generally, due to an error of the phase plate itself or an alignment error produced during the 45-deg. alignment operation with respect to the linearly polarized light, the circularly polarized light emerging from the phase difference place is not a perfect circular polarization light, but rather it is elliptically polarized light (approximately circularly polarized light). In this embodiment, in consideration of it, such apparatus errors can be removed by a specific measurement method and calculation.

First of all, without placing a sample on the light path, birefringence is measured in accordance with the method of the seventh embodiment. The measured birefringence is memorized in a memory, not shown. If there is no apparatus error, since a sample is absent there, no birefringence is measured such that the light detected is a perfect circular polarization light such as shown in FIG. 6A. If there is an apparatus error, due to this apparatus error the input light which should inherently be perfect circular polarization light is transformed into elliptically polarized light, such that the elliptical component would be measured as the birefringence. Here, the birefringence measured without a sample is denoted by s.

Subsequently, a sample is introduced into the light path, and the birefringence is measured. The birefringence obtained by this measurement is birefringence s' that is based on the birefringence c of the sample and also that contains the aforementioned birefringence s resulting from the apparatus error.

In the computing means, calculation is made on the basis of the birefringence s measured beforehand without a sample and the birefringence c' obtained by the measurement.

Generally, the Jones matrix C of a sample having birefringence c can be expressed as follows, where c is the phase difference in terms of unit radian:

$$C = \begin{pmatrix} \exp(-i\frac{c}{2}) & 0 \\ 0 & \exp(i\frac{c}{2}) \end{pmatrix}$$

Where $\xi$ is the difference between the apparatus error birefringence and the advance axis angle of the true birefringence of the sample, $R(\xi)$ is the coordinate transformation matrix by rotation, S is the Jones matrix of the apparatus error birefringence, C is the Jones matrix of the true birefringence of the sample, and C' is the Jones matrix of the birefringence containing the apparatus error, then there is a relation $$C' = CR(\xi)SR(-\xi)$$

Thus, by performing the following matrix operation at the computing circuit, the true birefringence without the birefringence produced by the apparatus error can be detected.

$$C = C'R(\xi)S^{-1}R(-\xi)$$

where $S^{-1}$ is the inverse matrix of S. In the above equation, a rotation matrix may be included in C and C'.

As described above, in accordance with the birefringence measuring apparatus of this embodiment, the birefringence can be measured at a high precision even if the light impinging on the sample is not a perfect circular polarization light.

It should be noted that the concept of the present embodiment is applicable to all the other embodiments described hereinbefore.

While the invention has been described with reference to the structures disclosed herein, it is not confined to the details set forth and this application is intended to cover such modifications or changes as may come within the purposes of the improvements or the scope of the following claims.

What is claimed is:
1. A birefringence measuring apparatus, comprising:
    a light projecting unit for projecting approximately circularly polarized light upon a sample;
    a Stokes meter for detecting a state of polarization of light from the sample; and
    calculating means for calculating birefringence of the sample on the basis of a Stokes parameter from said Stokes meter, wherein said calculating means calculate the following equations:

$$B = \frac{\pi}{2} - \arcsin\left(\frac{S_3}{S_0}\right)$$

$$\phi = -\frac{\pi}{4} + \frac{1}{2}\arctan\left(\frac{S_2}{S_1}\right)$$

where B is the amount of birefringence, $\phi$ is a phase advance axis angle, $S_0$-$S_3$ are Stokes parameters wherein $S_0$ is a total light quantity, $S_1$ is a horizontal linear polarization component, $S_2$ is a +45 degree linear polarization component, and $S_3$ is a right-handed circular polarized component.

2. An apparatus according to claim 1, wherein said light projecting unit includes a light source and converting means for converting light from the light source into approximately circularly polarized light.

3. An apparatus according to claim 2, wherein said converting means includes a phase difference plate.

4. An apparatus according to claim 2, wherein the light from the light source has a wavelength not greater than 370 nm.

5. An apparatus according to claim 2, wherein the light from the light source has a wavelength not greater than 200 nm.

6. An apparatus according to claim 1, further comprising a dividing unit including three optical elements having the same reflection characteristic and the same transmission characteristic.

7. An apparatus according to claim 1, further comprising a memory for memorizing birefringence measured by said birefringence measuring apparatus without a sample, wherein said calculating means calculates the birefringence of the sample also on the basis of the birefringence memorized in said memory.

* * * * *